United States Patent
Boss et al.

(10) Patent No.: US 12,161,664 B2
(45) Date of Patent: Dec. 10, 2024

(54) TETRATHIONATE FOR CYANIDE AND METHYLMERCAPTAN POISONING

(71) Applicants: The Regents of the University of California, Oakland, CA (US); The Regents of the University of Colorado, Denver, CO (US)

(72) Inventors: Gerry R. Boss, La Jolla, CA (US); Adriano Chan, La Jolla, CA (US); Matthew Brenner, Irvine, CA (US); Sari Brenner Mahon, Irvine, CA (US); Vikhyat Bebarta, Denver, CO (US)

(73) Assignees: The Regents of the University of California, Oakland, CA (US); The Regents of the University of Colorado, Denver, CO (US)

( * ) Notice: Subject to any disclaimer, the term of this patent is extended or adjusted under 35 U.S.C. 154(b) by 490 days.

(21) Appl. No.: 17/271,284

(22) PCT Filed: Aug. 20, 2019

(86) PCT No.: PCT/US2019/047200
§ 371 (c)(1),
(2) Date: Feb. 25, 2021

(87) PCT Pub. No.: WO2020/046635
PCT Pub. Date: Mar. 5, 2020

(65) Prior Publication Data
US 2021/0330702 A1   Oct. 28, 2021

Related U.S. Application Data

(60) Provisional application No. 62/723,641, filed on Aug. 28, 2018.

(51) Int. Cl.
*A61K 33/04* (2006.01)
*A61K 9/00* (2006.01)
*G01N 33/52* (2006.01)

(52) U.S. Cl.
CPC ............ *A61K 33/04* (2013.01); *A61K 9/0019* (2013.01); *A61K 9/0043* (2013.01); *G01N 33/52* (2013.01); *G01N 2800/709* (2013.01)

(58) Field of Classification Search
CPC .... A61K 33/04; A61K 9/0019; A61K 9/0043; G01N 33/52; G01N 2800/709
See application file for complete search history.

(56) References Cited

U.S. PATENT DOCUMENTS

| | | | |
|---|---|---|---|
| 2013/0136725 A1* | 5/2013 | Gojon-Romanillos | ....... A61K 45/06 424/94.1 |
| 2014/0120159 A1 | 5/2014 | Petrikovics et al. | |
| 2015/0064286 A1 | 3/2015 | Gojon-Romanillos et al. | |

OTHER PUBLICATIONS

T. F. Cummings, The treatment of cyanide poisoning, Occupational Medicine 2004;54:82-85 DOI: 10.1093/occmed/kqh020 (Year: 2004).*
Sodium Tetrathionate and Methylene Blue in Cyanide and Carbon Monoxide Poisoning J'ohn H. Draize: Science, New Series, vol. 78, No. 2016 (Aug. 18, 1933), p. 145 Published by: American Association for the Advancement of Science; https://www.jstor.org/stable/1660633 (Year: 1933).*
Acute Exposure Guideline Levels for Selected Airborne Chemicals: vol. 15; ISBN 978-0-309-29122-4; Committee on Acute Exposure Guideline Levels Committee on Toxicology Board on Environmental Studies and Toxicology; National Academies Press, 500 Fifth Street, NW, Keck 360, Washington, DC 20001; (Year: 2013).*
Susan M. DeLeon, Jason D. Downey, Diane M. Hildenberger, Melissa O. Rhoomes, Lamont Booker, Gary A. Rockwood, and Kelly A. Basi; DMTS is an effective treatment in both an inhalation and njection model for cyanide poisoning using unanesthetized mice; Clin Toxicol (Phila). May 2018 ; 56(5): 332-341. : (Year: 2018).*
PCT International Search Report and Written Opinion for PCT Application No. PCT/US2019/047200 mailed Nov. 22, 2019 (6 pages).
Baskin et al., "The Effect of Sodium Tetrathionate on Cyanide Convesion to Thiocyanate by Enzymatic and Non-enzymatic Mechanisms," Journal of Applied Toxicology, 1990, 10(5):379-382.
Draize, "Sodium Tetrathionate and Methylene Blue in Cyanide and Carbon Monoxide Poisoning," Sciences, '1933, 78(2016):45.
Koh et al., "Determination of Tetrathionate, Thiosulfate, Sulfite and Trithionate in Their Mixtures by Spectrophotometry," Analytical Sciences, 1989, 5:79-84.
Nietzel et al., "Spectrophotometric Determination of Tetrathionate," Analytical Chemistry, 1955, 27:1839-1841.

* cited by examiner

*Primary Examiner* — Robert A Wax
*Assistant Examiner* — Andre Mach
(74) *Attorney, Agent, or Firm* — Eversheds-Sutherland (US) LLP

(57) ABSTRACT

Provided is a method, and pharmaceutical composition, to treat or prevent cyanide poisoning and/or methylmercaptan poisoning comprising administering to a subject in need an effective amount of tetrathionate by intramuscular injection or by intranasal administration. Also provided is a method for detecting the presence of tetrathionate in a sample by reacting it with cyanide and measuring the resulting thiocyanate with ferric nitrate.

4 Claims, 12 Drawing Sheets

Anesthetic Injection Port

TETRATHIONATE FOR CYANIDE AND METHYLMERCAPTAN POISONING

CROSS REFERENCE TO RELATED APPLICATIONS

This application claims the priority benefit of PCT/US2019/047200 filed on Aug. 20, 2019 which claims the priority benefit to U.S. Provisional Patent Application No. 62/723,641, filed Aug. 28, 2018, the entire contents of which are incorporated herein by reference in their entirety.

GOVERNMENT SPONSORSHIP

This invention was made with government support under grant Nos. NS105057 and ES27698 awarded by the National Institutes of Health. The government has certain rights in the invention.

TECHNICAL FIELD

The present invention relates to treatments for cyanide and methylmercapatan (methanethiol) poisoning.

BACKGROUND

Cyanide is readily available in industrial settings and scientific laboratories, and can be prepared relatively easily from formamide and ammonia-methane mixtures. Thus, it has the potential to come into the hands of terrorists, and to be used as a weapon of mass destruction[5-7]. It would be particularly lethal in closed spaces such as subway and train stations, where a gaseous discharge could affect a large number of people.

Three antidotes are approved for cyanide poisoning in the U.S.—nitrites, sodium thiosulfate, and hydroxo-cobalamin (vitamin $B_{12a}$)[2, 8]. Currently available cyanide antidotes in the U.S. are hydroxocobalamin (marketed as Cyanokit®) and the combination of sodium nitrite and sodium thiosulfate (marketed as Nithiodote®). Both of these antidotes are given intravenously over 5-10 min, which is not practical in the setting of mass casualties as could occur in a major industrial accident or a terrorist attack. Nitrites generate NO and methemoglobin; the former displaces cyanide from cytochrome c oxidase and the latter has a high affinity for cyanide, but can no longer bind oxygen[8]. Thiosulfate acts as a sulfur donor for the enzyme rhodanese, which detoxifies cyanide by converting it to thiocyanate. Cobalamin detoxifies cyanide by binding it with a relatively high affinity[9]. Nitrites can be injected intravenously as sodium nitrite, or inhaled as amyl nitrite over several minutes; sodium thiosulfate and cobalamin are administered intravenously. Because of the time required to start an intravenous line or inhale amyl nitrite, these agents would not be useful in treating a large number of cyanide-exposed victims.

Sodium tetrathionate ($Na_2S_4O_6$) has the following structure:

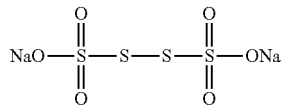

Cyanide reacts rapidly and directly with the innermost sulfur atoms through a reaction known as cyanolysis via the following scheme: $Na_2S_4O_6 + CN^- \rightarrow SCN^- + SO_4^{-2} +$ $Na_2S_2O_3$, where $SCN^-$ is thiocyanate, $SO_4^{-2}$ is sulfate, and $Na_2S_2O_3$ is sodium thiosulfate[11-13]. In vivo, the resulting thiosulfate moiety can serve as a substrate for rhodanese, neutralizing a second cyanide molecule. Tetrathionate was first shown to work as a cyanide antidote in rabbits in 1910[14]. Subsequent investigators showed that on a molar basis tetrathionate was 1.5-3.3-fold more potent than thiosulfate in rescuing mice, rats, and dogs from cyanide poisoning[15-21]. The approximate two-fold greater potency of tetrathionate is likely from neutralizing two moles of cyanide per mole, compared to one mole for thiosulfate.

SUMMARY OF THE INVENTION

In embodiments, the invention provides a method of treating or preventing cyanide poisoning comprising administering to a subject in need an effective amount of sodium tetrathionate by intramuscular injection.

In embodiments, the invention provides a method of treating or preventing cyanide poisoning comprising administering to a subject in need an effective amount of sodium tetrathionate by intranasal instillation.

In embodiments, the invention provides a method of preventing or treating methylmercaptan (methanethiol) poisoning comprising administering to a subject in need an effective amount of sodium tetrathionate by intramuscular injection.

In embodiments, the invention provides a method of preventing or treating methylmercaptan (methanethiol) poisoning comprising administering to a subject in need an effective amount of sodium tetrathionate by intranasal instillation.

In embodiments, the invention provides a method of measuring tetrathionate in a biological sample comprising reacting the biological sample with ferric nitrate and detecting a colorimetric change indicating the presence of tetrathionate in the sample.

In embodiments, the invention provides that the biological sample is human blood or plasma.

DETAILED DESCRIPTION

Figure 1:
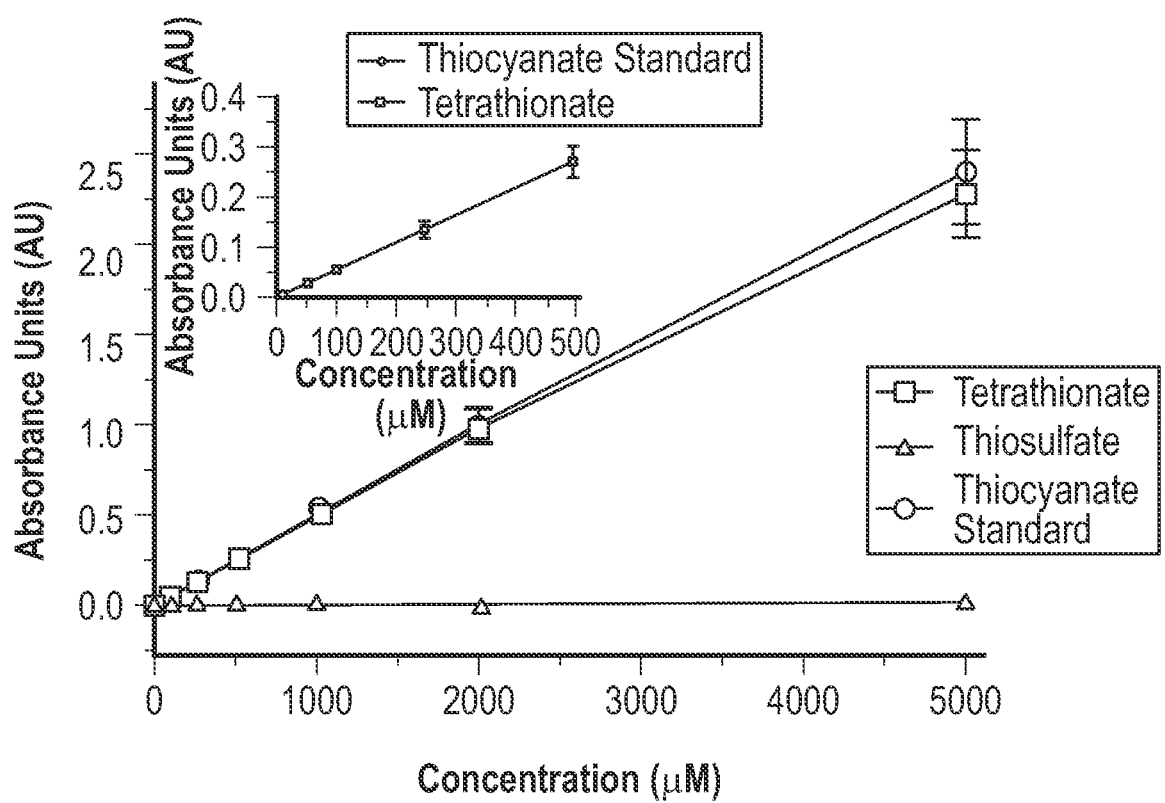
FIG. 1 shows measurement of tetrathionate by reaction with cyanide. Sodium tetrathionate at concentrations of 50 µM to 5 mM were incubated with a five-fold excess of cyanide for 15 min at 37° C. in 50 mM sodium phosphate, pH 11; thiocyanate was then measured by adding ferric nitrate and recording absorption at 460 nm. The main figure shows the full concentration range and the inset shows 50 to 500 µM. A thiocyanate standard was included (dashed line). Data are the mean of three experiments with error bars showing standard deviations; the square of the sample correlation coefficient, i.e., $r^2$ was 0.98. Thiosulfate did not react with cyanide, even after a 60 min incubation at a concentration of 5 mM.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates);

PCR: The Polymerase Chain Reaction (Mullis et al., eds., 1994); Remington, The Science and Practice of Pharmacy, 20th ed., (Lippincott, Williams & Wilkins 2003), and Remington, The Science and Practice of Pharmacy, 22th ed., (Pharmaceutical Press and Philadelphia College of Pharmacy at University of the Sciences 2012).

The present inventions provides, in embodiments, a method of treating or preventing cyanide poisoning comprising administering to a subject in need an effective amount of tetrathionate by intramuscular injection.

The present inventions provides, in embodiments, a method of treating or preventing cyanide poisoning comprising administering to a subject in need an effective amount of tetrathionate by intranasal instillation.

The present inventions provides, in embodiments, a method of treating or preventing methylmercaptan (methanethiol) poisoning comprising administering to a subject in need an effective amount of tetrathionate by intramuscular injection.

The present inventions provides, in embodiments, a method of treating or preventing methylmercaptan (methanethiol) poisoning comprising administering to a subject in need an effective amount of tetrathionate by intranasal administration.

Tetrathionate refers to the pharmaceutically active tetrathionate anion $S_4O^{2-}_6$, a sulfur oxoanion, which can be derived from the compound tetrathionic acid, $H_2S_4O_6$. In embodiments, tetrathionate can be formulated for administration as any pharmaceutically acceptable salt thereof, including but not limited to sodium, potassium and barium salts. As used in the claims, tetrathionate is intended to encompass tetrathionate anion and any pharmaceutically acceptable salt form thereof, such as but not limited to sodium tetrathionate. The invention contemplates the administration of a pharmaceutical composition comprising tetrathionate or pharmaceutically acceptable salts thereof. The invention further contemplates the use of mono-, di-, tri-, tetra-, hepta-, or hexa-thionates, and pharmaceutically acceptable salts thereof, formulated in a pharmaceutical composition.

In embodiments for intranasal administration, a pharmaceutical composition comprising tetrathionate is formulated for intranasal delivery and can be delivered for systemic administration by drops, sprays, aerosolized mists or powders, for example, to the sino-nasal mucosal membranes. In embodiments for intramuscular injection, a pharmaceutical composition comprising tetrathionate can be formulated for intramuscular delivery and delivered for systemic administration with a hypodermic needle or syringe, for example, activated either manually or autoinjected. In embodiments of the above inventions, the subject is a human. In embodiments, the effective amount of tetrathionate is about 0.5 to 50 mg/kg, or 1 to 25 mg/kg, or 2.5 to 10 mg/kg, or about 5.2 mg/kg.

In embodiments, the invention provides a method of measuring tetrathionate in a biological sample comprising reacting the biological sample with cyanide to produce thiocyanate, reacting the thiocyanate with ferric nitrate; and detecting a colorimetric change indicating the presence of tetrathionate in the sample.

In embodiments, the invention provides that the biological sample is human blood or plasma.

Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to a pharmaceutically acceptable composition, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to age-related eye diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

There are at least four unique aspects of the invention. First, sodium tetrathionate has been shown previously to rescue animals from cyanide poisoning, but, in all these studies, it was administered by intravenous injection only. The invention provides that tetrathionate is effective when administered by intramuscular injection. This is of some significance, because sodium thiosulfate, which is structurally similar to sodium tetrathionate and is also a cyanide antidote, has been reported not to be effective when administered by intramuscular injection. Thus, it was not to be expected that sodium tetrathionate would be effective after intramuscular injection. Second, the invention provides that sodium tetrathionate is an effective cyanide antidote when administered by intranasal instillation. The active tetrathionate moiety carries a double negative charge, and negatively-charged molecules generally do not cross cell membranes readily. Thus, it was not to be expected that sodium tetrathionate would be effective after intranasal instillation. Third, current methods of measuring tetrathionate lack sensitivity and specificity, and are not applicable to complex matrices such as blood. The invention provides a novel method to measure tetrathionate that is applicable to physiological fluids, and pharmacokinetic studies of tetrathionate after administering it to animals and humans. And fourth, the invention provides that sodium tetrathionate is also effective against methylmercaptan (methanethiol) poisoning. No antidotes currently exist against methylmercaptan, and thus this is an important finding. The invention provides one drug that is effective against two toxic chemicals.

Sodium tetrathionate neutralizes two moles of cyanide per mole of tetrathionate. The first mole of cyanide is neutralized through a direct non-enzymatic reaction, yielding thiocyanate—an essentially non-toxic compound. The invention provides that this reaction occurs under physiological conditions. In addition to thiocyanate, another product of the reaction is thiosulfate. The latter can then react with another mole of cyanide, via the enzyme rhodanese, thereby neutralizing a total of two moles of cyanide. The invention provides that tetrathionate also reacts directly with methylmercaptan, but it appears to neutralize only one mole of methylmercaptan per mole of tetrathionate.

The assay provided by the invention for measuring tetrathionate is dependent on tetrathioante's reaction with cyanide to generate thiocyanate. A sensitive and specific assay exists for measuring thiocyanate by reacting it with ferric nitrate, thereby generating a colored product. The assay provided by the invention is sensitive to micromolar concentrations of tetrathionate, whereas currently available methods for measuring tetrathionate can only measure millimolar concentrations.

EXAMPLES

Example 1

Tetrathionate's Reaction with Cyanide can be Used to Measure Tetrathionate

The main method used currently to measure tetrathionate is HPLC with ultraviolet detection at 230-260 nm[13, 35]; many compounds absorb at such low wavelengths and, in complex matrices such as plasma, will cause interference. Moreover, the molar extinction coefficient of tetrathionate is only $5 \times 10^2$ $M^{-1}$ $cm^{-1}$ at 260 nm, which means tetrathionate concentrations must be >1 mM to be measured accurately[35]. Older methods to measure tetrathionate relied on iodine titration, which is even less sensitive than HPLC[25]. It was hypothesized that tetrathionate's direct reaction with cyanide could be used to measure tetrathionate, because the end product of the reaction—thiocyanate (SCN)—is easily measured by a sensitive reaction with ferric nitrate[36]. To test this hypothesis, varying concentrations of tetrathionate were mixed with cyanide and compared the amount of the thiocyanate product to authentic thiocyanate. Thiocyanate was produced that was almost identical to a thiocyanate standard over a wide range of tetrathionate concentrations from 50 μM to 5 mM (FIG. 1; inset shows concentration range of 50 to 500 μM). The $pK_a$ of HCN is 9.3 and HCN's boiling point is 26° C. The experiment was conducted at pH 11 to be sure all of the cyanide was the CN$^-$ ion. In pilot experiments it was had shown that the high pH had no effect on measuring thiocyanate. As part of this experiment, thiosulfate was mixed with cyanide, and no thiocyanate production was found, even after long reaction times (FIG. 1). In addition to providing a method for measuring tetrathionate, this experiment shows that tetrathionate reacts readily with cyanide, whereas thiosulfate does not.

Measurement of Tetrathionate in Plasma

Figure 2:
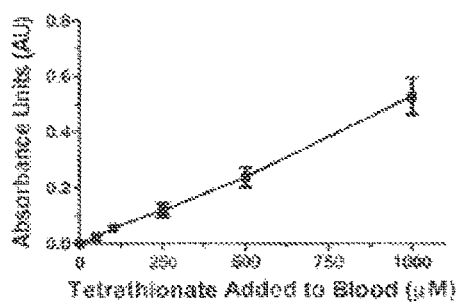
FIG. 2 shows measurement of tetrathionate in plasma. Sodium tetrathionate concentrations of 50 µM to 5 mM were added to human blood, and cells and plasma were separated by centrifugation. Plasma proteins were precipitated with perchloric acid, and the clarified supernatant was neutralized with potassium bicarbonate. Potassium cyanide was added to the samples, and thiocyanate was measured as described in FIG. 1. Data are the mean of three experiments with error bars showing standard deviations; $r^2 = 0.95$.
Figure 3:
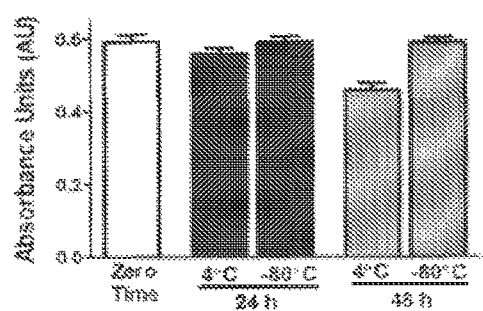
FIG. 3 shows tetrathionate stability in stored plasma. Sodium tetrathionate was added to whole blood, and then plasma was immediately separated from the cells and kept at either 4° or −80° C. for 24 or 48 h; tetrathionate was measured as described in FIG. 2. Data are the mean of three experiments with error bars showing standard deviations. Only the samples stored at 4° C. for 48 h were significantly different from the zero time samples as analyzed by a one-way ANOVA with a Dunett's post-test analysis ($p<0.05$).

As mentioned, current methods of measuring tetrathionate in blood or plasma lack sensitivity. The newly devised method of measuring tetrathionate was assessed for use with mammalian blood, and varying amounts of tetrathionate were added to animal or human blood in vitro, the cells and plasma were extracted separately, and tetrathionate was measured. It was found that the tetrathionate remained in the plasma, and that tetrathionate recovery was linear over a concentration range from 50 μM to 1 mM (FIG. 2; measured tetrathionate concentration is in absorbance units, but can be converted to concentration by comparison to thiocyanate standard in FIG. 1). Plasma thiocyanate concentrations are low (5-10 μM), yielding a low background in blank samples that was subtracted from measured values[37,38]. Similar results were found in serum, but the data were less reproducible, possibly because some tetrathionate was lost in the clot.

Figure 4:
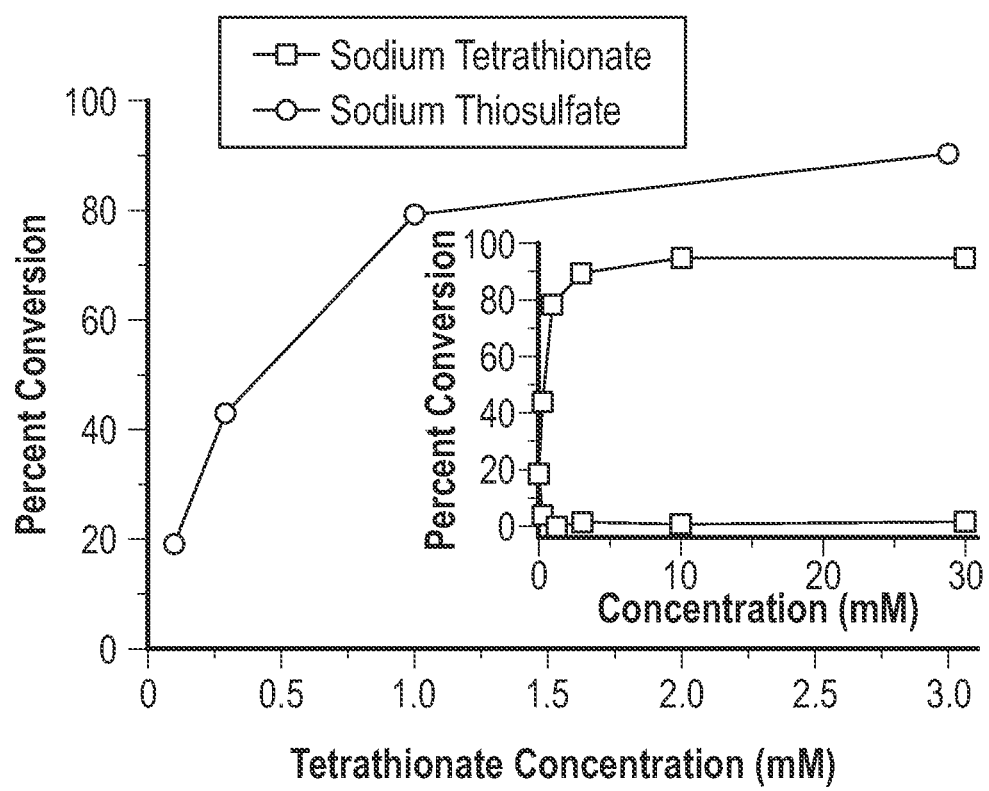
FIG. 4 shows tetrathionate reaction with cyanide under clinically-relevant conditions. Sodium tetrathionate at concentrations from 50 μM to 3 mM was incubated with 100 μM potassium cyanide for 15 min at 37° C. in 50 mM sodium phosphate, pH 11. The resulting thiocyanate was measured as described in FIG. 1. Inset shows sodium tetrathionate and sodium thiosulfate at concentrations from 50 μM to 30 mM. Similar results were obtained in two other experiments.

Reaction of Tetrathionate with Cyanide at Clinically-Relevant Cyanide Concentrations In the above experiments, relatively high cyanide concentrations were used so that the excess cyanide would drive all of the tetrathionate to thiocyanate. However, these experiments do not indicate whether tetrathionate will react with cyanide at concentrations that occur in cyanide-poisoned humans. To address this question, varying concentrations of tetrathionate were incubated with 100 μM cyanide, a generally lethal concentration in humans[39]. It was found that 1 mM tetrathionate converted 80% of the cyanide to thiocyanate, and that 3 mM tetrathionate converted 90% of the cyanide to thiocyanate (FIG. 4). Because of the previously noted volatility of HCN, these studies were conducted at an elevated pH, but, in other experiments using completely filled capped tubes with no gas headspace, it was shown that tetrathionate reacts with cyanide at physiological pH. Based on extrapolations from rabbit and pig data (presented below), the projected human tetrathionate dose will yield a plasma concentration of ~2 mM. Thus, at clinically-relevant cyanide and tetrathionate concentrations, tetrathionate would be expected to convert >80% of the cyanide to thiocyanate. As would be expected from the previous experiments, thiosulfate, even at a concentration as high as 30 mM, did not react with 100 μM cyanide (FIG. 4, inset).

Tetrathionate Absorption after Intramuscular Injection

Figure 5:
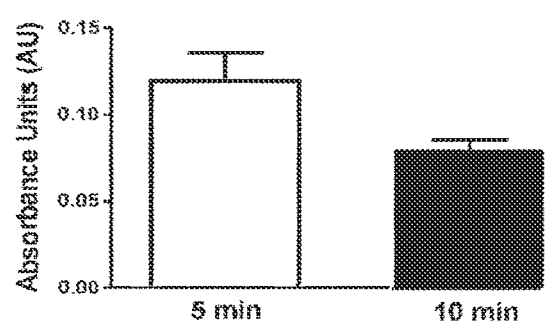
FIG. 5 shows tetrathionate absorption after intramuscular injection in mice. Mice were injected in the gastrocnemius muscle with 50 μl of 200 mM tetrathionate dissolved in water. The mice were euthanized either 5 or 10 min later, and blood was drawn from an intracardiac puncture. Plasma was separated from cells, and analyzed for tetrathionate as described in FIG. 2. The data are the means of three mice in each condition.

An effective way to administer a cyanide antidote in a mass casualty scenario is via intramuscular injection, but this requires the drug to be absorbed rapidly from the injection site. Sodium tetrathionate dissolved in water and injected intramuscularly in mice yielded higher plasma concentrations at 5 min than at 10 min, suggesting rapid absorption and relatively rapid clearance (FIG. 5). These studies were done in mice, and because of the small blood volume of mice and technical difficulties in drawing blood from mice, one mouse is required for each time point. The invention provides that 2 M tetrathionate is well absorbed after intramuscular injection.

Tetrathionate Efficacy as a Cyanide Antidote in Rabbits, Pigs and Mice

General Overview of Animal Models.

According to general HAZMAT principles, persons exposed to toxic chemicals should be evacuated immediately from the contaminated area, but it would be difficult to remove a large number of victims quickly from a confined, hard-to-access location such as a subway station. In these cases, it would be useful to treat the victims as quickly as possible, prior to or simultaneous with evacuation from the contaminated area. In consideration of these worse-case scenarios, animal models were developed that incorporate continued exposure to cyanide, even after treatment. This makes the models extremely rigorous, because the antidote has to neutralize not just the amount of cyanide that triggered treatment—cardiovascular and respiratory collapse in rabbits and pigs, respectively—but also cyanide that continued to be administered to a profoundly sick animal.

Overview of Rabbit and Pig Models.

The heart and central respiratory center are major cyanide targets, and the inventors sought to determine if tetrathionate could rescue animals from both cardiovascular and respiratory collapse. Since it would be technically difficult to have a single model for both endpoints, separate models in rabbits and pigs were developed. Rabbits have a relatively high metabolic rate and can sustain only very short periods of apnea—providing a short treatment window; they, therefore, are not a good model for respiratory collapse and cardiovascular collapse was used as the trigger for treatment in rabbits. Since pigs can sustain longer periods of apnea, respiratory collapse was used as the trigger for treatment in pigs. Due to their sheer size, it is difficult to expose rabbits and pigs to cyanide gas safely, and cyanide salt was infused intravenously at a constant rate. Since the $pK_a$ of HCN is 9.2, cyanide exists almost exclusively as HCN at physiological pH, and infusing a cyanide salt generates HCN, the inhaled form of cyanide absorbed from the lungs. Thus, a cyanide infusion model yields the same end product as an inhalation model.

Rabbit Model.

Figure 6:
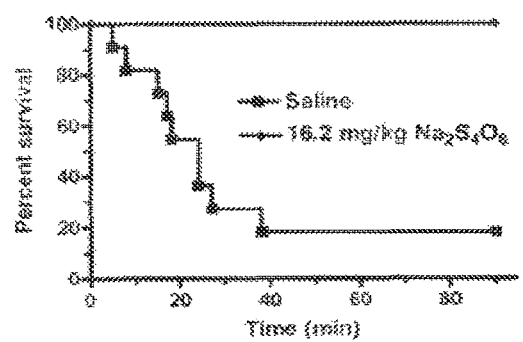
FIG. 6 shows tetrathionate rescues rabbits from cyanide poisoning. New Zealand White male rabbits five to six months old and weighing ~4 kg received a continuous intravenous infusion of sodium cyanide until their mean arterial pressure was <70% of baseline. They were then injected in the right pectoral muscle with 0.15 ml of 1.5 M sodium tetrathionate, and the cyanide infusion was continued for an additional 30 min. Surviving animals were euthanized at 90 min. The difference between the tetrathionate-treated animals and saline-treated animals was significantly different by a log rank test ($p<0.01$).

Rabbits are anesthetized with ketamine and xylazine, and mechanically ventilated. Sodium cyanide is injected intravenously at 0.08 mg/kg/min, and when the mean arterial blood pressure measured by an intra-arterial catheter decreases to <70% of baseline, the animals are injected intramuscularly with antidote. The cyanide infusion is continued an additional 30 min, and the animals are then observed for 60 min more. In addition to hemodynamic monitoring, tissue concentrations of oxy- and deoxyhemoglobin are monitored by diffuse optical spectroscopy; this provides a real-time measure of cyanide inhibition of cytochrome c oxidase, since mitochondrial respiration accounts for >95% of tissue oxygen consumption, reflected in tissue oxy- and deoxyhemoglobin concentrations[41]. This model leads to >80% mortality in control animals (9 of 11 animals died), whereas six of six animals treated with 16.2 mg/kg sodium tetrathionate survived (FIG. 6; difference in survival between saline- and tetrathionate-injected animals was significant at p<0.001 by a log rank test). The human equivalent dose would be 5.2 mg/kg[42].

Pig Model.

Figure 7:
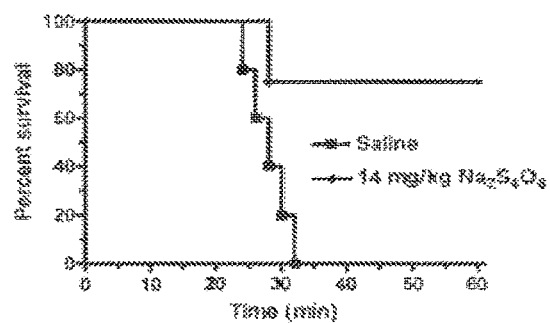
FIG. 7 shows tetrathionate rescues pigs from cyanide poisoning. Non-ventilated Yorkshire female pigs four to five months old and weighing ~50 kg received a continuous intravenous infusion of 0.17 mg/kg/min potassium cyanide. On average, the animals became apneic after 8 min and the cyanide infusion was continued for 1 min beyond onset of apnea. At the time the cyanide infusion was stopped, the animals were injected in the right vastus medials muscle with 1.0 ml of 2 M sodium tetrathionate. Five control and four treated animals were studied. The difference between the tetrathionate-treated animals and saline-treated animals was significantly different by a log rank test ($p<0.01$).

Pigs are anesthetized with isoflurane, but not ventilated. Potassium cyanide is infused intravenously at a rate of 0.17 mg/kg/min until 1 min beyond the onset of apnea, defined as no breathing for 20 sec as determined by capnography[43]. Simultaneous with stopping the cyanide infusion, the pigs are injected with antidote into the right vastus medialis muscle. This model is 100% lethal, and three of four pigs treated with 18 mg/kg sodium tetrathionate survived (FIG. 7; difference in survival between treated and untreated animals was significant by a log rank test at p<0.001).

Mouse Model.

Figure 8A:
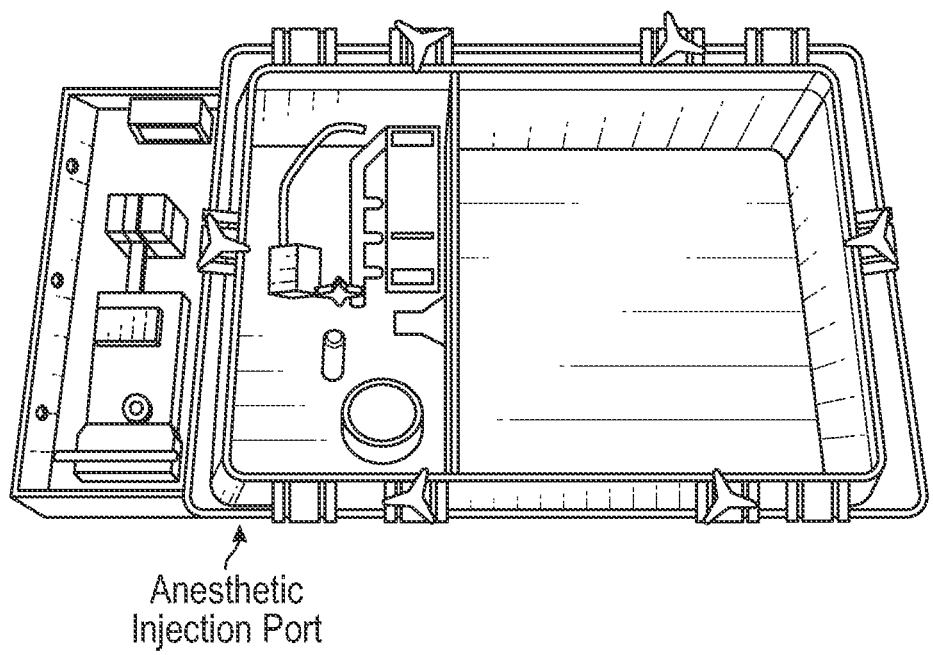
FIG. 8 shows mouse gas exposure chamber. Photograph (A) and schematic (B) of chamber. The chamber maintains a constant HCN gas concentration at a controlled temperature using a rapid circulation system. Compartment A is the animal section, which holds up to four mice, but generally exposing one mouse at a time. It is separated from compartment B by a fine plastic grate. Mounted on the grate is a circulation fan with heater, which maintains the temperature at 30±0.5° C. Compartment C houses the electronics. Separate ports are used for (i) injecting liquid isoflurane, (ii) injecting KCN into a beaker containing sulfuric acid, and (iii) gas sampling. Using the above model, we found that 40, 80 and 135 mg/kg sodium tetrathionate increased survival in a dose-dependent manner from a lethal exposure to HCN (FIG. 10). The survival curves for all three sodium tetrathionate doses were significantly different from saline-injected animals as analyzed by a log rank test ($p<0.05$ using Prism 5 software).
Figure 8B:
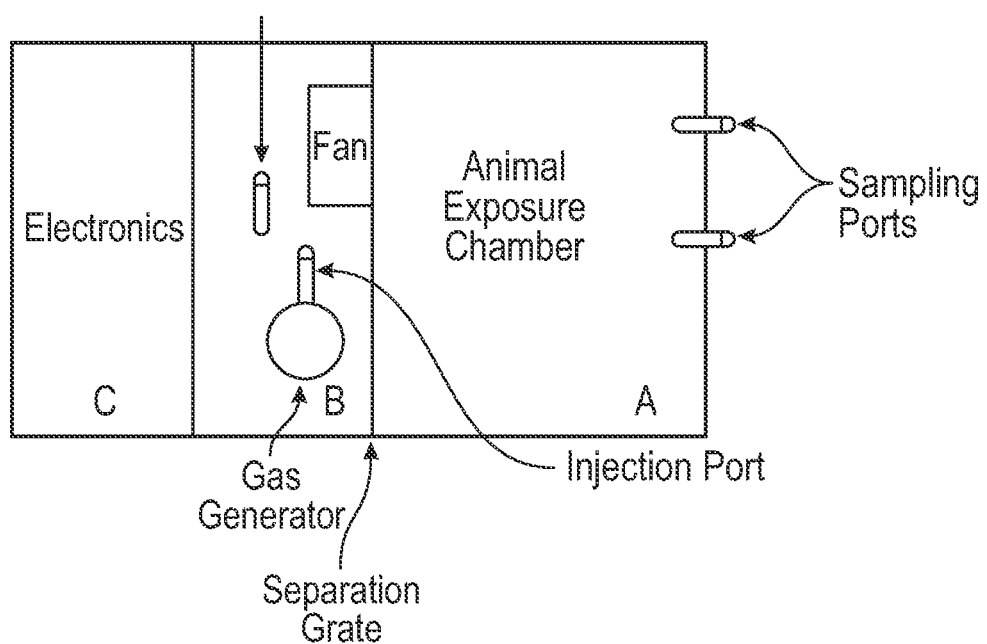
Figure 9:
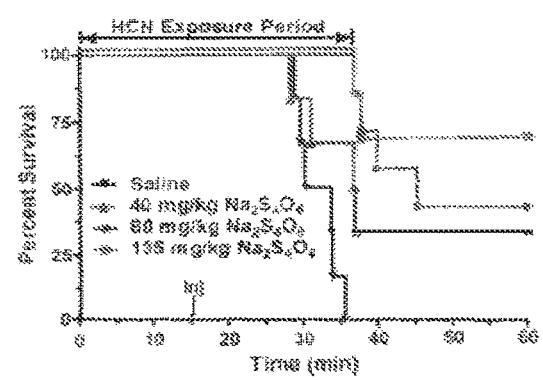
FIG. 9 shows tetrathionate rescues mice from cyanide poisoning. C57Bl/6J male mice 12-16 weeks old were exposed to 587 ppm HCN gas for 40 min in a sealed gas chamber. The HCN is generated by injecting KCN into a beaker of sulfuric acid; it reaches equilibrium within 5 min of KCN injection, and remains stable throughout the exposure period 44. After 15 min of gas exposure, the mice were removed from the chamber, and injected (Inject) with saline or the indicated amounts of sodium tetrathionate. Surviving animals were removed from the chamber at 40 min. Six animals were studied per condition. Three different tetrathionate doses were tested; all three doses were significantly different from saline-treated animals by a log rank test ($p<0.05$).
Figure 10:
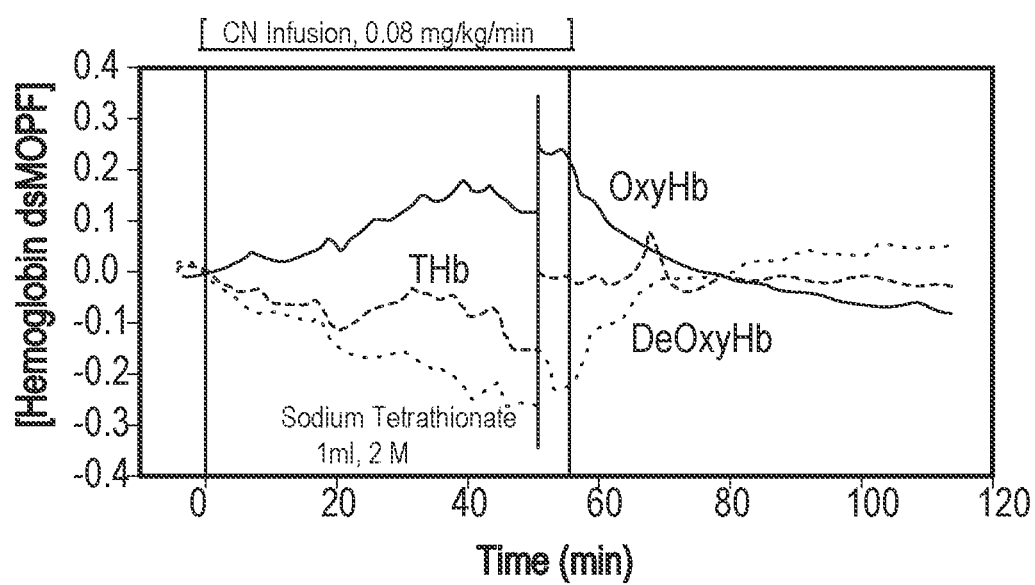
FIG. 10 shows reversal of cyanide poisoning in rabbits by intranasal instillation of 1 ml 2 M sodium tetrathionate. Cyanide poisoning was followed by diffuse optical spectroscopy, which assesses the tissue concentrations of oxy- and deoxyhemoglobin. Due to cyanide inhibition of mitochondrial respiration, tissue oxyhemoglobin increases (red line in figure) and tissue deoxyhemoglobin decreases (blue line in figure) as cyanide poisoning progresses. Sodium tetrathionate was administered by intranasal instillation at the time noted by the blue vertical line Immediately after the tetrathionate instillation, tissue oxyhemoglobin and deoxyhemoglobin concentrations returned to baseline, indicating rapid and complete reversal of cyanide poisoning. Total hemoglobin concentration (THb) was also followed (green line).
Figure 11:
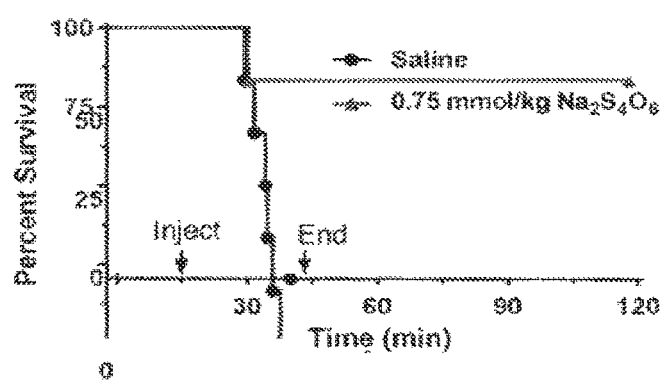
FIG. 11 shows tetrathonate rescue of mice from methylmercaptan (methanethiol) poisoning. The model is similar to cyanide poisoning, except that methylmercaptan gas is generated in the exposure chamber shown in FIG. 8 by adding sodium methylmercaptan to sulfuric acid, thereby generating methylmercaptan gas. Exposure begins at zero time and then the mice were removed from the gas chamber after 15 min and injected intramuscularly with sodium tetrathionate. The mice were exposed to methylmercaptan gas for a total of 40 min as indicated by the arrow that indicates "End." All six saline-injected animals died prior to completion of the methylmercaptan exposure, whereas five of six tetrathionate-injected animals survived. The difference between the two groups was statistically different by a log rank test ($p<0.01$).

Mice are small enough that they can be exposed to cyanide gas within a sealed chamber; this minimizes the risk of exposing laboratory personnel to cyanide, but it allows only for visual monitoring of the animals (FIG. 8). The mice are exposed to the gas for 15 min, injected with test antidote in the gastrocnemius muscle, and then re-exposed to the gas for 25 min. This model assumes about 15 min are required for emergency medical personnel to arrive at a disaster scene, and another 25 min are required to treat and evacuate the victims. As required by our Institutional Animal Care and Use Committee (IACUC), the mice are anesthetized by injecting isoflurane into the chamber to a final concentration of 2%; at 30° C., the isoflurane rapidly vaporizes and anesthetizes the mice.

Tetrathionate Safety

Sodium tetrathionate is lethal in rabbits and dogs at doses of 100 and 500 mg/kg, respectively[25,26]. Sodium tetrathionate was tested in mice, and found to be tolerated at doses up to 900 mg/kg, although scaling from a mouse to a human is difficult, the human equivalent dose is 73 mg/kg.

REFERENCES (1) Salkowski A A, Penney D G. Cyanide poisoning in animals and humans: a review. Vet Hum Toxicol 1994; 36(5):455-66.
(2) Gracia R, Shepherd G. Cyanide poisoning and its treatment. Pharmacotherapy 2004; 24(10):1358-65.
(3) Way J L. Cyanide intoxication and its mechanism of antagonism. Annu Rev Pharmacol Toxicol 1984; 24:451-81.
(4) Scheffler I E. Mitochondria make a come back. Advanced Drug Delivery Reviews 49, 3-26. 2001.
(5) Greenfield R A, Brown B R, Hutchins J B, Iandolo J J, Jackson R, Slater L N, Bronze M S. Microbiological, biological, and chemical weapons of warfare and terrorism. Am J Med Sci 2002; 323(6):326-40.
(6) Rotenberg J S. Cyanide as a weapon of terror. Pediatr Ann 2003; 32(4):236-40.
(7) Eckstein M. Cyanide as a chemical terrorism weapon. JEMS 2004; 29(8):suppl-31.
(8) Cummings T F. The treatment of cyanide poisoning. Occup Med (Lond) 2004; 54(2):82-5.
(9) Hayward G C, Hill H A O, Pratt J M, Vanston N J, Williams A R W. The chemistry of vitamin B(12). Part IV.1 The thermodynamic trans-effect. J Chem Soc 1965; 6485-93.
(10) Bebarta V S, Britain M, Chan A, Garrett N, Yoon D, Burney T, Mukai D, Babin M, Pilz R B, Mahon S B, Brenner M, Boss G R. Sodium nitrite and sodium thiosulfate are effective against acute cyamide poisoning when administered by intramuscular injection. Manuscript submitted for publication 2016.
(11) Kelly D P, Chambers L A, Trudinger P A. Cyanolysis and spectrophotometric estimation of trithionate in mixture with thiosulfate and tetrathionate. Anal Chem 1969; 41:898-901.
(12) Eremenko R R K, Brodsky A I. Study of the reactions of the polythionates by means of tagged sulfur. II. Reactions of the tetrathionates and the pentathionates. J Gen Chem, Moscow 1955; 25:1189-96.
(13) Ji C, Yan X, Horvath A K, Pan C, Zhao Y, Gao Q. Comprehensive simultaneous kinetic study of sulfitolysis and thiosulfatolysis of tetrathionate ion: unravelling the unique pH dependence of thiosulfatolysis. J Phys Chem A 2015; 119(8):1238-45.
(14) Hebting J. Versuche uberentgiftung der blansäure durch schwefelabspaltende substanzen. Biochemische Zeitschrift 1910; 28:208-12.
(15) Chistoni A, Foresti B. L'antidotismo del tetrationato sodico nelle intossicazioni da acido cianidrico. Arch Internat de Pharmacod 1932; 42:140-71.
(16) Binet L, Wellers G, Dubrisay J. Contribution à l'étude de l'intoxication cyanhydrique, valeur antidote du tétrathionate de sodium. C R Acad Sci 1948; 226:1941-4.

(17) Biset L, Wellers G, Dubrisay J. Sur le mécanisma de l'action antidote du tétrathionate de sodium, vis-à-vis de l'intoxication cyanhydrique. C R Acad Sci 1949; 228: 1781-3.

(18) Binet L, Wellers G, Dubrisay J. Value and mechanism of the antidote action of sodium tetrathionate in hydrocyanic poisoning. Presse Med 1951; 59(32):641-3.

(19) Nitescu Ii, Craiu R, Wassermann N. Cyanides and anticyanides. The action of sodium tetrathionate as an antidote in hydrocyanic poisoning. Rum Med Rev 1961; 5:203-4.

(20) Chen K K, Rose Cl, Clowes G H A. Comparative values of several antidotes in cyanid poisoning. Am J Med Sci 1937; 188:767-81.

(21) Hatch R C, Laflamme D P, Jain A V. Effects of various known and potential cyanide antagonists and a glutathione depletor on acute toxicity of cyanide in mice. Vet Hum Toxicol 1990 February; 32(1):9-16.

(22) Theis F V, Freeland M R. Thromboangitis obliterans. Treatment with sodium tetrathionate and sodium thiosulfate. Arch Surg 1940; 40:190-207.

(23) Theis F V, Freeland M R. Thrombo-angiitis obliterans: clinical observations and arterial blood oxygen studies during treatment of the disease with sodium tetrathionate and sodium thiosulfate. Ann Surg 1941; 113(6):1107-8.

(24) Supplemental report on sodium tetrathionate. J Am Med Assoc 1947; 134:1092-3.

(25) Gilman A, Philips F S., The metabolic reduction and nephrotoxic action of tetrathionate in relation to a possible interaction with sulfhydryl compounds. Am J Physiol 1946; 147:115-26.

(26) Sloan H. Production of experimental uremia by sodium tetrathionate. Proc Soc Exp Biol Med 1951; 76(2):344-6.

(27) Philips F S, Gilman A., The effect of tetrathionate in vivo and in vitro on the activity of succinoxidase. J Biol Chem 1947; 167(1):209-17.

(28) Bloom N, Forbes G, Policoff L. Toxicity of sodium tetrathionate. Proc Soc Exp Biol Med 1949; 72(1):207-9.

(29) Rechetzki K F, Henneberg R, da Silva P H, do Nascimento A J. Reference values for methemoglobin concentrations in children. Rev Bras Hematol Hemoter 2012; 34(1):14-6.

(30) Calabrese E J, Moore G S, Ho S C. Low erythrocyte glucose-6-phosphate dehydrogenase (G-6-PDH) activity and susceptibility to nitrite-induced methemoglobin formation. Bull Environ Contam Toxicol 1980; 25(6):837-40.

(31) Sherman C, Lepine A J, Smith C N, Wirtz K R, Schulze E. Sodium nitrite-containing pharmaceutical compositions. U.S. Pat. No. 8,568,793 B2, 2013.

(32) Sherman C, Smith C M, Wirtz K R, Schulze E. Sodium thiosulfate-containing pharmaceutical compositions. U.S. Pat. No. 8,496,973 2013.

(33) David N A. The pharmacology of dimethyl sulfoxide. Annu Rev Pharmacol 1972; 12:353-74.

(34) Ramirez E, Luza S. Dimethyl sulfoxide in the treatment of mental patients. Ann N Y Acad Sci 1967; 141(1):655-67.

(35) Varga D, Horvath A K. Kinetics and mechanism of the decomposition of tetrathionate ion in alkaline medium. Inorg Chem 2007; 46(18):7654-61.

(36) Korpilande T, Heliovaara M, Knekt P, Marniemi J, Aromaa A, Aho K. Smoking history and serum cotinine and thiocyanate concentrations as determinants of rheumatoid factor in non-rheumatoid subjects. Rheumatology (Oxford) 2004; 43(11):1424-8.

(37) Hasuike Y, Nakanishi T, Moriguchi R, Otaki Y, Nanami M, Hama Y, Naka M, Miyagawa K, Izumi M, Takamitsu Y. Accumulation of cyanide and thiocyanate in haemodialysis patients. Nephrol Dial Transplant 2004; 19(6): 1474-9.

(38) Michigami Y, Takahashi T, He F R, Yamamoto Y, Ueda K. Determination of thiocyanate in human serum by ion chromatography. Analyst 1988; 113(3):389-92.

(39) Baud F J, Barriot P, Toffis V, Riou B, Vicaut E, Lecarpentier Y, Bourdon R, Astier A, Bismuth C. Elevated blood cyanide concentrations in victims of smoke inhalation. N Engl J Med 1991, 325(25):1761-6.

(40) Zhang H, Jeffrey M I. A kinetic study of rearrangement and degradation reactions of tetrathionate and trithionate in near-neutral solutions. Inorg Chem 2010; 49(22): 10273-82.

(41) Lee J, Kim J G, Mahon S B, Mukai D, Yoon D, Boss G R, Patterson S E, Rockwood G, Isom G, Brenner M. Noninvasive optical cytochrome c oxidase redox state measurements using diffuse optical spectroscopy. J Biomed Opt 2014; 19(5):055001.

(42) U S Department of Health and Human Services F. Estimating the maximum safe starting dose in initial clinical trials for therapeutics in adult healthy volunteers. Guidance for Industry 2005; 1-27.

(43) Bebarta V, Tanen D, Boudrea S, Castaneda M, Zarzabal L, Vargas T, Boss G. Intravenous cobinamide versus hydrocobalamin for acute treatment of severe cyanide poisonong in a swine (Suc Scroba) model. Ann Emerg Med 2014; 64:612-9.

(44) Chan A, Balasubramanian M, Blackledge W, Mohammad O M, Alvarez L, Boss G R, Bigby T D. Cobinamide is superior to other treatments in a mouse model of cyanide poisoning. Clin Toxicol (Phila) 2010; 48:709-17.

(45) Chan A, Crankshaw D L, Monteil A, Patterson S E, Nagasawa H T, Briggs J E, Kozocas J A, Mahon S B, Brenner M, Pilz R B, Bigby T D, Boss G R. The combination of cobinamide and sulfanegen is highly effective in mouse models of cyanide poisoning. Clin Toxicol (Phila) 2011; 49(5):366-73.

(46) Chan A, Jiang J, Fridman A, Guo L T, Shelton G D, Liu M T, Green C, Haushalter K J, Patel H H, Lee J, Yoon D, Burney T, Mukai D, Mahon S B, Brenner M, Pilz R B, Boss G R. Nitrocobinamide, a new cyanide antidote that can be administered by intramuscular injection. J Med Chem 2015; 58(4):1750-9.

(47) Brenner M, Mahon S B, Lee J, Kim J, Mukai D, Goodman S, Kreuter K A, Ahdout R, Mohammad O, Sharma V S, Blackledge W, Boss G R. Comparison of cobinamide to hydroxocobalamin in reversing cyanide physiologic effects in rabbits using diffuse optical spectroscopy monitoring. J Biomed Opt 2010; 15(1):017001.

(48) Brenner M, Kim J G, Mahon S B, Lee J, Kreuter K A, Blackledge W, Mukai D, Patterson S, Mohammad O, Sharma V S, Boss G R. Intramuscular Cobinamide sulfite in a rabbit model of sublethal cyanide toxicity. Ann Emerg Med 2009; 55:352-62.

(49) Kim J C, Lee J, Mahon S B, Mukai D, Patterson S E, Boss G R, Tromberg B J, Brenner M. Noninvasive monitoring of treatment response in a rabbit cyanide toxicity model reveals differences in brain and muscle metabolism. J Biomed Optics 2012; 17.

(50) Bebarta V S, Tanen D A, Lairet J, Dixon P S, Valtier S, Bush A. Hydroxocobalamin and sodium thiosulfate versus sodium nitrite and sodium thiosulfate in the treatment of acute cyanide toxicity in a swine (Sus scrofa) model. Ann Emerg Med 2010; 55(4):345-51.

(51) Bebarta V S, Pitotti R L, Dixon P, Lairet J R, Bush A, Tanen D A. Hydroxocobalamin versus sodium thiosulfate for the treatment of acute cyanide toxicity in a swine (*Sus scrofa*) model. Ann Emerg Med 2012; 59(6):532-9.
(52) Borron S W, Stonerook M, Reid F. Efficacy of hydroxocobalamin for the treatment of acute cyanide poisoning in adult beagle dogs. Clin Toxicol (Phila) 2006; 44 Suppl 1:5-15.
(53) Hirsch L, Byron K, Gibney M. Intramuscular risk at insulin injection sites—measurement of the distance from skin to muscle and rationale for shorter-length needles for subcutaneous insulin therapy. Diabetes Technol Ther 2014; 16(12):867-73.
(54) Blackledge W C, Blackledge C W, Griesel A, Mahon S B, Brenner M, Pilz R B, Boss G R. New facile method to measure cyanide in blood. Anal Chem 2010; 82(10):4216-21.
(55) Ma J, Dasgupta P K, Blackledge W, Boss G R. Temperature dependence of Henry's law constant for hydrogen cyanide. Generation of trace standard gaseous hydrogen cyanide. Environ Sci Technol 2010; 44(8): 3028-34.
(56) Rumanian Medical Review 5: 203-204, 1961.
(57) Am J. Med Sci, 188: 767-781, 1937.
(58) La Presse Medicale 59: 641-643, 1951.
(59) Vet Hum Toxicol 32: 9-16, 1990.
(60) C.R. Acad Sci 226: 1941-1944m, 1948.
(61) C.R. Acad. Sci. 228: 1781-1783, 1949.
(62) Arch. Int. Pharmacol Ther. 42: 140-172, 1932.
(63) Inorg Chem 49: 10273-10282, 2010.
(64) J. Phys. Chem A 119: 1238-1245, 2015.
(65) Inorg Chem 50: 9670-9677, 2011.
(66) Inorg Chem 46: 7654-7661, 2007.
(67) Inorg Chem 49: 10273-10282, 2010.
(68) Am J Physiol 147: 115-126, 1946.

What is claimed is:

1. A method of treating cyanide poisoning in a human subject comprising administering to a human subject in need an effective amount of tetrathionate by intranasal instillation, wherein the effective amount is 0.5 to 50 mg/kg.

2. The method of claim 1, wherein the effective amount is 1 to 25 mg/kg.

3. The method of claim 1, wherein the effective amount is 2.5 to 10 mg/kg.

4. The method of claim 1, wherein the effective amount is about 5.2 mg/kg.

* * * * *

UNITED STATES PATENT AND TRADEMARK OFFICE
CERTIFICATE OF CORRECTION

| | | |
|---|---|---|
| PATENT NO. | : 12,161,664 B2 | Page 1 of 1 |
| APPLICATION NO. | : 17/271284 | |
| DATED | : December 10, 2024 | |
| INVENTOR(S) | : Gerry R. Boss et al. | |

It is certified that error appears in the above-identified patent and that said Letters Patent is hereby corrected as shown below:

In the Specification

Column 1, Lines 15-18, please replace the paragraph under the GOVERNMENT SPONSORSHIP from "This invention was made with government support under grant Nos. NS105057 and ES27698 awarded by the National Institutes of Health. The government has certain rights in the invention." to --This invention was made with government support under NS058030, NS087964, and NS105057 awarded by the National Institutes of Health. The government has certain rights in the invention.--

Signed and Sealed this
Third Day of February, 2026

John A. Squires
*Director of the United States Patent and Trademark Office*